United States Patent
Kulma et al.

(10) Patent No.: US 8,101,047 B2
(45) Date of Patent: Jan. 24, 2012

(54) METHOD OF CORRECTING GYPSUM CRYSTAL WATER EFFECT ON INFRARED MOISTURE MEASUREMENT

(75) Inventors: Unto Kulma, Vantaa (FI); Jaakko Olavi Uusalo, Klaukkala (FI); Antti Paavola, Tampere (FI); Johanna Hansen, Kingston (CA); Gertjan Hofman, Vancouver (CA)

(73) Assignee: Honeywell International Inc., Morristown, NJ (US)

( * ) Notice: Subject to any disclaimer, the term of this patent is extended or adjusted under 35 U.S.C. 154(b) by 301 days.

(21) Appl. No.: 12/560,763

(22) Filed: Sep. 16, 2009

(65) Prior Publication Data

US 2010/0078139 A1    Apr. 1, 2010

Related U.S. Application Data

(60) Provisional application No. 61/101,137, filed on Sep. 29, 2008.

(51) Int. Cl.
*D21H 17/67* (2006.01)
*D21F 7/00* (2006.01)
*G01N 23/06* (2006.01)

(52) U.S. Cl. ............. 162/181.2; 162/181.3; 162/198; 700/128; 700/129; 378/51; 378/53

(58) Field of Classification Search ........... 162/181.2, 162/181.3, 192, 198, 252, 253, 258, 259, 162/262; 378/44, 45, 46, 51, 53; 700/127, 700/128, 129; 73/73
See application file for complete search history.

(56) References Cited

U.S. PATENT DOCUMENTS

| | | | | |
|---|---|---|---|---|
| 3,660,662 A | * | 5/1972 | Puolakka | 378/45 |
| 4,815,116 A | | 3/1989 | Cho | |
| 4,845,730 A | * | 7/1989 | Mercer | 378/53 |
| 4,879,471 A | | 11/1989 | Dahlquist | |
| 5,014,288 A | | 5/1991 | Chase et al. | |
| 5,094,535 A | | 3/1992 | Dahlquist | |
| 5,166,748 A | | 11/1992 | Dahlquist | |
| 5,853,543 A | | 12/1998 | Hu | |
| 5,854,821 A | * | 12/1998 | Chase et al. | 378/53 |
| 5,892,679 A | | 4/1999 | He | |
| 6,059,931 A | | 5/2000 | Hu | |
| 6,080,278 A | | 6/2000 | Heaven | |
| 6,092,003 A | | 7/2000 | Hagart-Alexander | |
| 6,149,770 A | | 11/2000 | Hu | |
| 6,466,839 B1 | | 10/2002 | Heaven | |
| 6,717,148 B2 | | 4/2004 | Kansakoski et al. | |
| 6,805,899 B2 | | 10/2004 | MacHattie | |
| 7,291,856 B2 | | 11/2007 | Haran | |
| 7,321,425 B2 | | 1/2008 | Haran | |
| 7,376,215 B2 | | 5/2008 | Hofman | |
| 7,382,456 B2 | | 6/2008 | Tixier | |
| 7,399,971 B2 | | 7/2008 | Hofman et al. | |

* cited by examiner

*Primary Examiner* — Eric Hug
*Assistant Examiner* — Peter Chin
(74) *Attorney, Agent, or Firm* — Cascio Schmoyer & Zervas

(57) ABSTRACT

Ash composition measurements of calcium carbonate and gypsum in paper is accomplished with a dual X-ray sensor system with one X-ray source that is powered at about 5.9 KV and a second X-ray source that is powered at about 4.2 KV. Corresponding detectors measure radiation from the respective X-ray sources that is emitted from the paper. Data derived from the measurements yields the gypsum and crystal water content in the paper. The dual X-ray sensor system can be employed in conjunction with infrared total moisture measurements of paper products being manufactured on a paper-making making machine, which contain gypsum and calcium carbonate, in order to correct for the gypsum crystal water effect.

13 Claims, 2 Drawing Sheets

METHOD OF CORRECTING GYPSUM CRYSTAL WATER EFFECT ON INFRARED MOISTURE MEASUREMENT

REFERENCE TO RELATED APPLICATIONS

This application claims priority to U.S. Provisional Application 61/101,137 that was filed on Sep. 29, 2008.

FIELD OF THE INVENTION

The present invention generally relates to sensors and methods for measuring the moisture content in paper products and particularly to techniques for measuring the levels of gypsum, which contains crystal water, in order to determine the amount of "free" water that is present in the paper products especially paper products that also contain calcium carbonate.

BACKGROUND OF THE INVENTION

In the manufacture of paper on continuous papermaking machines, a web of paper is formed from an aqueous suspension of fibers (stock) on a traveling mesh papermaking fabric and water drains by gravity and suction through the fabric. The web is then transferred to the pressing section where more water is removed by pressure and vacuum. The web next enters the dryer section where steam heated dryers and hot air completes the drying process. The paper machine is, in essence, a water removal, system. A typical forming section of a papermaking machine includes an endless traveling papermaking fabric or wire, which travels over a series of water removal elements such as table rolls, foils, vacuum foils, and suction boxes. The stock is carried on the top surface of the papermaking fabric and is de-watered as the stock travels over the successive de-watering elements to form a sheet of paper. Finally, the wet sheet is transferred to the press section of the papermaking machine where enough water is removed to form a sheet of paper.

Paper is generally made of three constituents: water, wood pulp fiber, and ash. "Ash" is defined as that portion of the paper which remains after complete combustion. In particular, ash may include various mineral components such as calcium carbonate ($CaCO_3$), titanium dioxide ($TiO_2$), and clay (a major component of clay is $SiO_2$). Paper manufacturers use fillers such clay, titanium dioxide and calcium carbonate to enhance printability, color and other physical characteristics of the paper. Because of its low cost, paper manufacturers are also adding gypsum ($CaSO_4 2H_2O$) as filler, especially in combination with calcium carbonate. The dihydrated water is commonly referred to as "crystal" water. Gypsum loses its associated water molecules when it heated to a temperature of about 200° C.

It is conventional to measure the moisture content of sheet material upon its leaving the main dryer section or at the take up reel employing scanning sensors. Such measurements may be used to adjust the machine operation toward achieving desired parameters. One technique for measuring moisture content is to utilize the absorption spectrum of water in the infrared (IR) region. A monitoring or gauge apparatus for this purpose is commonly employed. Such an apparatus conventionally uses either a fixed gauge or a gauge mounted on a scanning head which is repetitively scanned transversely across the web at the exit from the dryer section and/or upon entry to the take up reel, as required by the individual machines. IR moisture measuring devices do not distinguish "free" water that is present in paper products from "crystal" water, in other words, IR moisture measurements yield a moisture content that is the sum of the free water and crystal water. It is desirable to obtain on-line measurements of the free water content.

The total amount of ash in paper and the composition of the ash are controlled by setting the rates of flow of gypsum and other ash components as well as the flow of wood pulp fiber and water to the papermaking system. The resulting sheet is periodically sampled and burned in the laboratory to determine the composition and amount of ash in the sheet. In the laboratory, the paper is burned under predetermined conditions and the resulting ash is accurately weighed and chemically analyzed. The papermaking parameters can then be altered based upon the resulting measurements. However, this procedure of manual control suffers from the main disadvantage that it is time consuming, even when the gypsum is the only ash component used. Thus, large quantities of paper which do not meet specifications may be manufactured while the laboratory tests are being conducted. The art is in search of improved on-line moisture sensing techniques for measuring the free water content of paper products that include gypsum.

SUMMARY OF THE INVENTION

The present invention is directed to techniques for correcting for gypsum crystal water effect, on infrared moisture measurements, that can be obtained directly from analysis of X-ray absorption spectra of paper products that contain both calcium carbonate and gypsum ($CaSO_4 2H_2O$). The invention is based in part on the discovery of a unique X-ray spectrum that enables the measurement and determination of the amount of gypsum that is present even in the presence of calcium carbonate. In particular, it has been demonstrated that an X-ray system that employs dual X-ray sensors operating at different known X-ray spectra, one spectra being sensitive to the total ash quantity that is present in the paper product and the second spectra being primarily sensitive to gypsum, yields accurate calculations of the amount of gypsum that is present. The level of crystal water can be readily derived from the gypsum content.

In one aspect, the invention is directed to dual X-ray sensors that include (i) a first X-ray source for directing first X-rays through a first portion of the paper product wherein the first X-rays source is powered by a first voltage power supply that powers the first X-ray source at a voltage of about 5.9 KV and corresponding means for detecting first X-rays that are transmitted through the first position on the paper product and generating a first signals indicative of the amount of first X-rays detected and (ii) a second X-ray source for directing second X-rays through a second portion of the paper product wherein the second X-rays source is powered by a second voltage power supply that powers the second X-ray source at a voltage of about 4.2 KV and corresponding means for detecting second X-rays that are transmitted through the second portion of the paper product and generating second signals indicative of the amount of second X-rays detected.

The dual X-ray sensor system can be employed to compute the amount of crystal (non-free) moisture in paper which contains both gypsum and calcium carbonate. In particular, in the manufacture of paper, the on-line infrared total moisture measurements of the paper products are corrected for the gypsum crystal water effect to yield free moisture measurements.

DETAILED DESCRIPTION OF PREFERRED EMBODIMENTS

Figure 1:
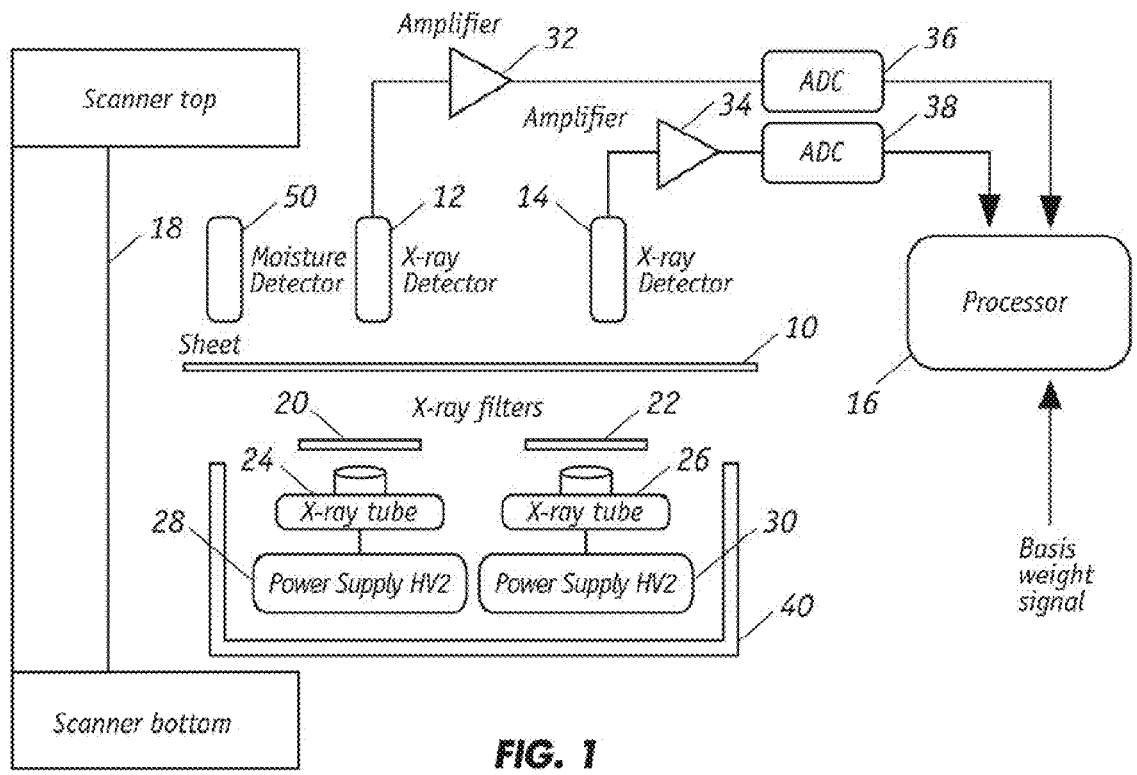
FIG. 1 illustrates a system that employs dual X-ray gauges (sensors) for on-line gypsum measurements.

The present invention is directed to a non-contact, on-line sensor system for measuring the free moisture content of paper products that contain gypsum. The sensor system is particularly suited for incorporation into industrial paper making machines. FIG. 1 illustrates a sensor system for measuring the free water content in paper sheet 10 which contains gypsum. The system includes dual X-ray absorption measurement devices that operate at different wavelengths: (1) ash X-ray sensor includes X-ray tube 24, that is powered by a fixed high voltage power supply 28, and a corresponding X-ray detector 12, and (2) the gypsum X-ray sensor includes X-ray tube 26, that is powered by a fixed high voltage power supply 30, and a corresponding X-ray detector 14. A radiation shield 40 partially encloses the dual X-ray sensors. The system preferably includes a scanner device 18 that moves the sensors across sheet 10 with the X-ray tubes 24 and 26 positioned on one side of sheet 10 and the corresponding X-ray detectors (or receivers) 12 and 14 positioned on the opposite side. The space between the X-ray tubes and detectors defines a measurement gap.

The fixed high voltage power supplies 28 and 30 are used to generate X-rays at selected energies. The fixed high voltage supply powers total ash X-ray tube 24 at a voltage so that X-rays generated are sensitive to both gypsum and calcium carbonate. Preferably this voltage is maintained at about 5.9 KV. For the gypsum X-ray sensor, the Fixed high voltage supply powers X-ray tube 26 at a voltage so that the X-rays generated are sensitive to primarily gypsum. Preferably, this voltage is maintained at about 4.3 KV. X-ray filters 12 and 14, in the form of aluminum plate, for example, can be employed to enhance the composition analysis.

In operation, X-rays from X-ray tubes 20 and 22 that are transmitted through sheet 10 are received by X-ray detectors 12 and 14, respectively. Simultaneously, detector 12 generates analog signals that are transmitted through amplifier 32 and analog-to-digital converter 36 to computer processor 16. Similarly, detector 14 generates analog signals that are transmitted through amplifier 34 and analog-to-digital converter 38 to processor 16.

Figure 2:
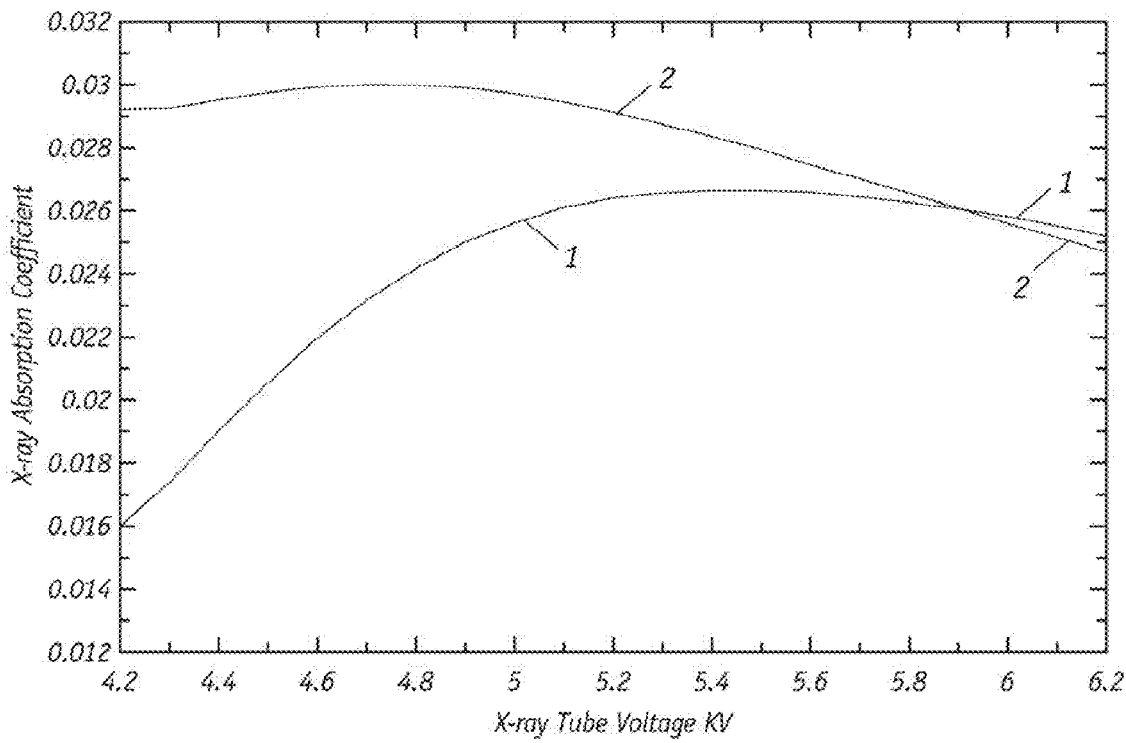
FIG. 2 is a graph of calculated X-ray absorption curves showing the absorption coefficients for pure calcium carbonate and for gypsum vs. applied voltage to X-ray tube.

The effective absorption coefficient for calcium carbonate (curve 1) and gypsum (curve 2) were measured at a spectral region of about 4.2 to 6.2 KV and the results are shown in FIG. 2. An X-ray gauge consisting of a conventional X-ray tube and corresponding detector with no aluminum filter was used. As is apparent, there is a cross over point at about 5.9 KV and there is almost a factor 2 difference in absorption region below about 4.2 KV. Thus, in a preferred embodiment, the first (or ash) X-ray sensor operates at 5.9 KV and the second (or gypsum) X-ray sensor operates at 4.2 KV. Processor 16 correlates the weighted sum of transmittance measurements to the amount of gypsum wherein the sum-coefficients are given by a fit to laboratory data.

Specifically, processor 16 initially calculates the relative readings for each X-ray sensor, which is defined by the relationship: $R=V/V_o$, where V is the measured detector response when the sheet is in place and $V_o$ is the measured detector response with no sheet in the measurement gap. This sensor ratio R is then employed to calculate the gypsum fraction using the following relationship:

$$CaSO_4 2H_2O \% = a\ Ln(R_h)/BW_n + b\ Ln(R_l)/BW_n + c$$

where $BW_n$ is the total mass of the sheet and $R_h$, $R_l$ are the ratios for X-ray sensor set to the higher (h) and the lower (l) voltage and (a, b, c) are constants to be determined by comparing to chemical laboratory data.

Figure 3:
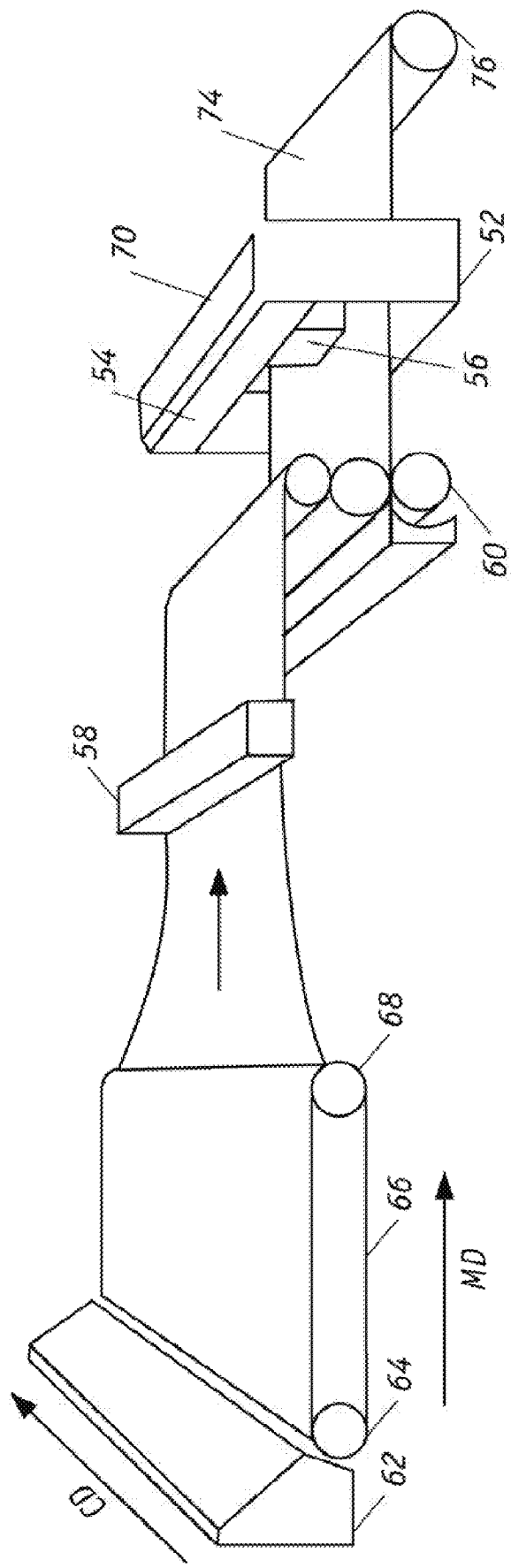
FIG. 3 illustrates a sheetmaking system incorporating the dual X-ray gauges of the present invention.

The dual X-ray sensor is particularly suited for use in a papermaking machine such as that illustrated in FIG. 3. The sheetmaking system for producing a continuous sheet of paper material 44 includes a headbox 62, a steambox 58, a calendaring stack 60, a take-up reel 76 and scanner system 70 that includes the inventive dual X-ray sensors. In the headbox 62, actuators are arranged to control discharge of wetstock onto supporting wire or web 66 along the cross direction. The sheet of fibrous material that forms on top of the wire 66 is trained to travel in the machine direction between rollers 64 and 68 and passes through a calendaring stack 60. The calendaring stack 60 includes actuators that control the compressive pressure applied across the paper web. The sheetmaking system includes a press section (not shown) where water is mechanically removed from the sheet and where the web is consolidated. Thereafter, water is removed by evaporation in the dryer section (not shown). The finished sheet product 74 is collected on a reel 76. In practice, the portion of the paper making process near a headbox is referred to as the "wet end", while the portion of the process near a take-up reel is referred to as the "dry end".

The scanner system 70 generally includes pairs of horizontally extending guide tracks 54 that span the width of the paper product 74. The guide tracks are supported at their opposite ends by upstanding stanchions 52 and are spaced apart vertically by a distance sufficient to allow clearance for paper product 74 to travel between the tracks. The dual X-ray sensors are secured to a carriage 56 that moves back-and-forth over to paper product 74 as measurements are made. On-line scanning sensor systems for papermaking manufacture are disclosed in U.S. Pat. No. 4,879,471 to Dahlquist, U.S. Pat. No. 5,094,535 to Dahlquist et al., and U.S. Pat. No. 5,166,748 to Dahlquist, all of which are incorporated herein fully by reference.

The dual X-ray sensors can be employed to adjust water measurements to account for the presence of gypsum crystal water in order to determine the free water content of paper products. On-line moisture measurements are typically obtained by infrared detectors that are positioned at various locations in the papermaking process in the machine direction and/or cross direction. For example, moisture detector 50 (FIG. 1) can also be secured to carriage 56 of the scanner system 70 (FIG. 3.). Suitable moisture detection devices are described, for example, U.S. Pat. No. 7,382,456 to Tixier et al., U.S. Pat. No. 7,321,425 to Haran, and U.S. Pat. No. 7,291,856. to Haran et al., which are incorporated herein by reference. Once the free water content is calculated, operating parameters of the papermaking machine can be adjusted, if necessary, should the water profile deviate from normal. Suitable control process is described in U.S. Pat. No. 6,092,003 to Hagart-Alexander which is incorporated herein by reference. Both dry end parameters, e.g., temperature of heating devices, and wet end parameters, e.g., wet stock water content and filler content, can be controlled to achieve the desired final product. Process control techniques for papermaking machines are further described, for instance, in U.S. Pat. No. 6,805,899 to MacHattie et al., U.S. Pat. No. 6,466,839 to Heaven et al., U.S. Pat. No. 6,149,770, to Hu et al., U.S. Pat. No. 6,092,003 to Hagart-Alexander et. al, U.S. Pat. No.

6,080,278 to Heaven et al., U.S. Pat. No. 6,059,931 to Hu et al. U.S. Pat. No. 5,853,543 to Hu et al., and U.S. Pat. No. 5,892,679 to He, which are all incorporated herein by reference.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A method of determining the amount of free water that is in a paper product that includes both gypsum and calcium carbonate fillers, which comprises the steps of:
   (a) measuring the amount of total water that is in the paper product;
   (b) calculating the amount of crystal water that is in the paper product by a process that comprises the steps of:
      (i) irradiating a first position on the paper product with a first X-ray having a known X-ray spectra which is sensitive to both gypsum and calcium carbonate;
      (ii) detecting the amount of first X-rays emitted from the paper product;
      (iii) irradiating a second position on the paper product with a second X-ray having a known X-ray spectra which is primarily sensitive to gypsum;
      (iv) detecting the amount of second X-rays emitted from the paper product; and
      (v) determining the amount of gypsum in the paper product; and
      (vi) deriving the amount of crystal water that is present in the paper product on the basis of the amount of gypsum that is in the paper product; and
   (c) reducing the amount of total water by the amount of crystal water to yield the free water amount that is in the paper product.

2. The method of claim 1 wherein step (a) employs an infrared radiation moisture detector.

3. The method of claim 1 wherein step (i) comprises directing first X-rays from a first X-ray source through a first position on the paper product wherein the first X-rays source is powered by a first voltage power supply that powers the first X-ray source at a voltage whereby the first X-rays generated are sensitive to both gypsum and calcium carbonate; and step (iii) comprises directing second X-rays from a second X-ray source through a second position on the paper product wherein the second X-rays source is powered by a second voltage power supply that powers the second X-ray source at a voltage whereby the second X-rays generated are sensitive primarily to gypsum.

4. The method of claim 3 wherein the first voltage power supply powers the first X-ray source at a voltage of about 5.9 KV and the second voltage power supply powers the second X-ray source at a voltage of about 4.2 KV.

5. The method of claim 1 wherein the paper product comprises paper that is being continuously manufactured in a paper making machine.

6. The method of claim 3 further comprising scanning the first X-ray source and the second X-ray source over the paper product.

7. A method of controlling the formation of a sheet of paper product from wet stock, comprising fibers and ash including calcium carbonate and gypsum, wherein the wet stock is formed on a water permeable wire moving in a papermaking machine that has a headbox through which wet stock is introduced onto the wire, said method comprising the steps of:
   (a) operating the machine and measuring the free water content of the paper product;
   (b) measuring the amount of total water that is in the paper product;
   (c) calculating the amount of free water that is in the paper product by a process that comprises the steps of:
      (i) irradiating a first position on the paper product with a first X-ray having a known X-ray spectra which is sensitive to both gypsum and calcium carbonate;
      (ii) detecting the amount of first X-rays emitted from the paper product;
      (iii) irradiating a second position on the paper product with a second X-ray having a known X-ray spectra which is primarily sensitive to gypsum;
      (iv) detecting the amount of second X-rays emitted from the paper product; and
      (v) determining the amount of gypsum in the paper product; and
      (vi) deriving the amount of crystal water that is present in the paper product on the basis of the amount of gypsum that is in the paper product;
   (d) reducing the amount of total water by the amount of crystal water to yield the free water amount that is in the paper product; and
   (e) adjusting operation of the papermaking machine in response to changes in the free water amount that is in the paper product.

8. The method of claim 7 wherein step (e) comprises adjusting the water content of the wet stock that is introduced from the headbox onto the wire.

9. The method of claim 7 wherein step (b) employs an infrared radiation moisture detector.

10. The method of claim 7 wherein step (i) comprises directing first X-rays from a first X-ray source through a first position on the paper product wherein the first X-rays source is powered by a first voltage power supply that powers the first X-ray source at a voltage whereby the first X-rays generated are sensitive to both gypsum and calcium carbonate; and step (iii) comprises directing second X-rays from a second X-ray source through a second position on the paper product wherein the second X-rays source is powered by a second voltage power supply that powers the second X-ray source at a voltage whereby the second X-rays generated are sensitive primarily to gypsum.

11. The method of claim 10 wherein the first voltage power supply powers the first X-ray source at a voltage of about 5.9 KV and the second voltage power supply powers the second X-ray source at a voltage of about 4.2 KV.

12. The method of claim 7 wherein step (ii) and (iv) operate simultaneously.

13. The method of claim 10 further comprising scanning the first X-ray source and the second X-ray source over the paper product.

* * * * *